(12) United States Patent
Pribula et al.

(10) Patent No.: US 11,759,628 B2
(45) Date of Patent: Sep. 19, 2023

(54) INSULATED ELECTRODE FOR DELIVERING TUMOR TREATING ELECTROMAGNETIC FIELDS

(71) Applicant: LifeBridge Innovations, PBC, Longwood, FL (US)

(72) Inventors: Martin A. Pribula, Mound, MN (US); Cory Michael Gloe, Minneapolis, MN (US); Jacob Edward Gefroh, Bloomington, MN (US); Andrew David Dahl, Circle Pines, MN (US); John Richard Haley, Osceola, WI (US); Peter F. Travers, Longwood, FL (US); Richard Rotondo, Oviedo, FL (US); Nathaniel R. Travers, Longwood, FL (US); Ken Watkins, Lake Mary, FL (US)

(73) Assignee: LifeBridge Innovations, PBC, Longwood, FL (US)

( * ) Notice: Subject to any disclaimer, the term of this patent is extended or adjusted under 35 U.S.C. 154(b) by 0 days.

(21) Appl. No.: 17/457,961

(22) Filed: Dec. 7, 2021

(65) Prior Publication Data
US 2022/0176102 A1 Jun. 9, 2022

Related U.S. Application Data

(60) Provisional application No. 63/123,009, filed on Dec. 9, 2020.

(51) Int. Cl.
*A61N 1/36* (2006.01)
*A61N 1/04* (2006.01)

(52) U.S. Cl.
CPC ....... *A61N 1/0484* (2013.01); *A61N 1/36002* (2017.08)

(58) Field of Classification Search
CPC .............. A61N 1/0484; A61N 1/36002; A61N 1/0476; A61N 1/36034; A61N 1/0408
See application file for complete search history.

(56) References Cited

U.S. PATENT DOCUMENTS

| 8,764,675 | B2 | 7/2014 | Palti | |
|---|---|---|---|---|
| 11,083,383 | B1 * | 8/2021 | Wu | .......... A61B 5/316 |
| 2009/0076366 | A1 * | 3/2009 | Palti | ...... A61N 1/0476 600/395 |

(Continued)

*Primary Examiner* — Ankit D Tejani
*Assistant Examiner* — Joshua Brendon Solomon
(74) *Attorney, Agent, or Firm* — Taylor IP, P.C.

(57) ABSTRACT

A tumor treating system for the delivery of tumor treating electric fields to a patient including a control device, a field generator, and electrodes. The control device has a frequency range, a firing configuration and a firing sequence. The field generator generates electrical signals within the frequency range. The electrodes are placed in optimized locations on the patient. Each electrode includes a ceramic layer, a metalized layer and a circuit element. The metalized layer is coupled to the ceramic layer on one side of the ceramic layer. The metalized layer has an outer surface facing away from the ceramic layer. The circuit element is coupled to the metalized layer. The coupling of the circuit element to the metalized layer is across substantially all of the outer surface of the metalized layer. The circuit element conducts the electrical signals to the metalized layer as directed by the control device.

16 Claims, 15 Drawing Sheets

(56) References Cited

U.S. PATENT DOCUMENTS

| | | | |
|---|---|---|---|
| 2016/0022986 A1* | 1/2016 | Travers | A61N 1/40 607/148 |
| 2021/0196348 A1* | 7/2021 | Wasserman | A61N 1/36002 |

\* cited by examiner

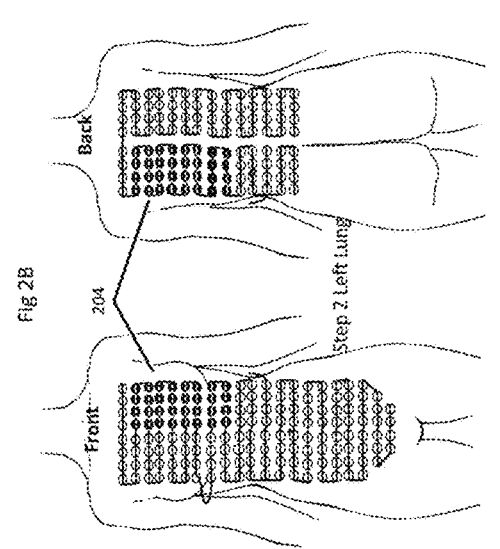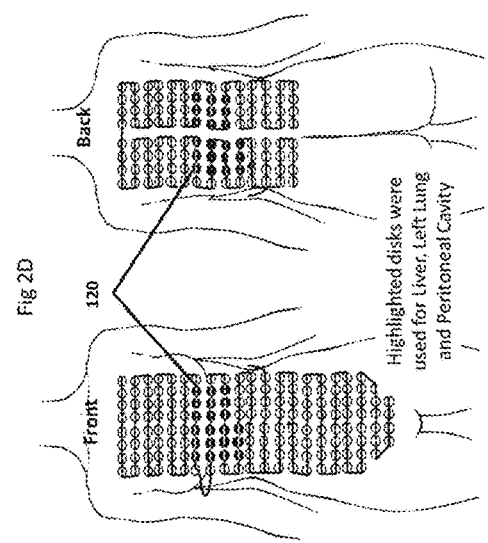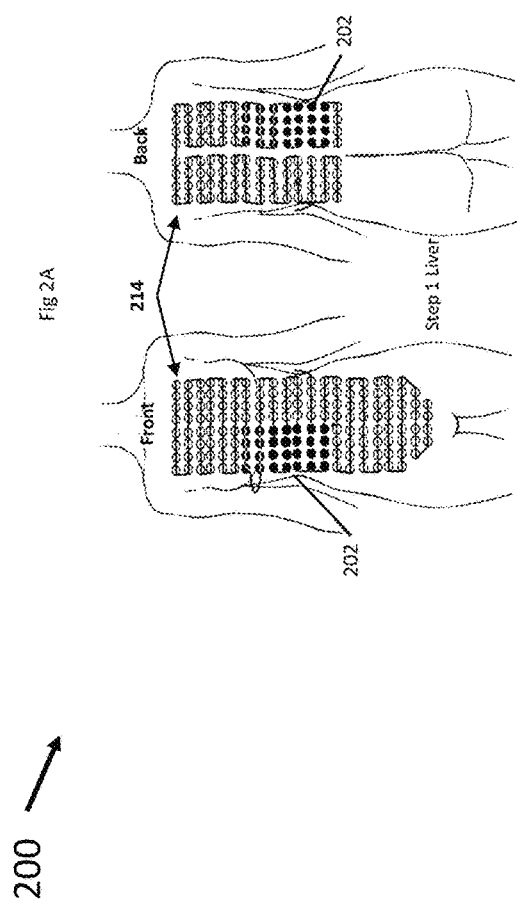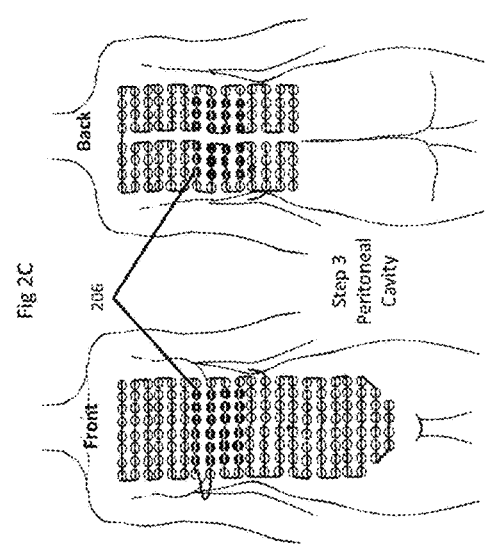

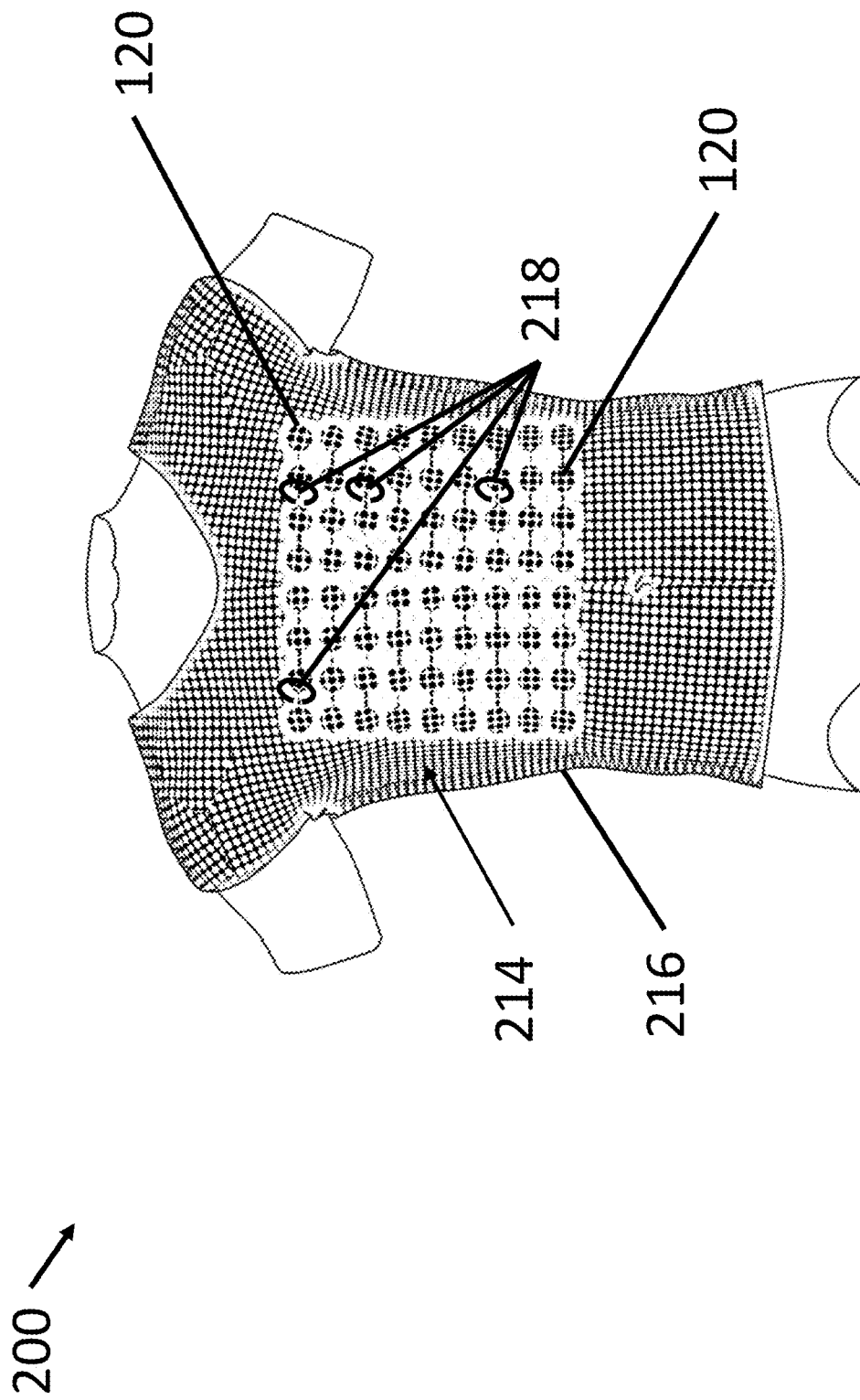

INSULATED ELECTRODE FOR DELIVERING TUMOR TREATING ELECTROMAGNETIC FIELDS

CROSS REFERENCE TO RELATED APPLICATIONS

This is a non-provisional patent application based upon U.S. provisional patent application Ser. No. 63/123,009, entitled "INSULATED ELECTRODE FOR DELIVERING TUMOR TREATING ELECTROMAGNETIC FIELDS", filed Dec. 9, 2020.

BACKGROUND OF THE INVENTION

1. Field of the Invention

The present invention relates to electrodes used for tumor and cancer cell treatment and more specifically to treatments involving the application of electromagnetic fields by way of the electrodes.

2. Description of the Related Art

Alternating Electric Fields, also referred to as Tumor Treating Fields (TTF's), can be employed as a type of cancer treatment therapy by using low-intensity electromagnetic fields. These low-intensity fields rapidly change direction, thousands of times per second. Since the TTF's are electric fields, they do not cause muscle twitching or severe adverse side effects on other electrically activated tissues. The growth rate of metastatic diseases is typically greater than the growth rate of normal, healthy cells. Alternating Electric Fields therapy takes advantage of this high growth-rate characteristic, by killing the cells as they reproduce. TTF's act to disrupt a cancer cell's mitotic process and cytokinesis by manipulating the cell's polarizable intracellular constituents, namely tublins that form mitotic spindles that pull the genetic material in the nucleus into two sister cells. TTF's interrupt mitotic spindle microtubule assembly thereby preventing cell division. The metastatic disease cells treated using TTF's will go into programmed cell death usually within 4 to 5 hours. The result is a significant reduction in tumor size and potential for full elimination of solid tumors. TTF's are tuned to treat specific cancer cells and thereby do not damage normal cells. TTF therapy can be used as a sole treatment method, or it can be combined with conventional drug delivery mechanisms.

TTF's are applied to patients using insulated electrodes located on the surface of the body of a patient. There are multiple configurations of insulated electrodes, but all have an insulated material with a high dielectric constant on one side and a thin metal coating on the other. Insulated electrodes used to generate TTF's always come in pairs with both sides being similar, but not necessarily the same.

What is needed in the art is an electrode that reduces the temperature experienced by the patient.

SUMMARY OF THE INVENTION

The present invention provides an electrode for an improved cancer and tumor treatment regime.

The invention in one form is directed to a tumor treating system for the delivery of tumor treating electric fields to a patient including a control device, a field generator, and electrodes. The control device has a frequency range, a firing configuration and a firing sequence. The field generator generates electrical signals within the frequency range. The electrodes are placed in optimized locations on the patient. Each electrode includes a ceramic layer, a metalized layer and a circuit element. The metalized layer is coupled to the ceramic layer on one side of the ceramic layer. The metalized layer has an outer surface facing away from the ceramic layer. The circuit element is coupled to the metalized layer. The coupling of the circuit element to the metalized layer is across substantially all of the outer surface of the metalized layer. The circuit element conducts the electrical signals to the metalized layer as directed by the control device.

The invention in another form is directed to an electrode used with a tumor treating system for the delivery of tumor treating electric fields to a patient. Each electrode includes a ceramic layer, a metalized layer and a circuit element. The metalized layer is coupled to the ceramic layer on one side of the ceramic layer. The metalized layer has an outer surface facing away from the ceramic layer. The circuit element is coupled to the metalized layer. The coupling of the circuit element to the metalized layer is across substantially all of the outer surface of the metalized layer. The circuit element conducts the electrical signals to the metalized layer as directed by the control device.

The invention in another form is directed to a method of using electrodes to deliver tumor treating electric fields to a patient including the steps of placing, programing and generating. The placing step places a plurality of the electrodes in optimized locations on the patient, each of the electrodes being independently programmable. The optimized locations are selected relative to a target area wherein at least one tumor is located. Each electrode includes a ceramic layer, a metalized layer and a circuit element. The metalized layer is coupled to the ceramic layer on one side of the ceramic layer. The metalized layer having an outer surface facing away from the ceramic layer. The circuit element is coupled to the metalized layer, the coupling of the metalized layer to the circuit element being across substantially all of the outer surface of the metalized layer, the circuit element conducting the electrical signals from the field generator to the metalized layer as directed by the control device. The programming step programs a control device with a frequency range, a firing configuration and a firing sequence for the plurality of electrodes. The generating step generates electrical signals in the frequency range, the electrical signals being directed to at least two of the electrodes in a sequence determined by the firing sequence.

An advantage of the present invention is that the electrodes have a high thermal conductivity due to their construct.

Another advantage of the present invention is that it allows for less warming of a patient's skin from individual electrodes.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 2A shows a selected subarray from a master array of FIG. 1 to apply an electric field over the liver of a subject;

FIG. 2B shows a selected subarray from a master array of FIG. 1 to apply an electric field over the left lung of a subject;

FIG. 2C shows a selected subarray from a master array of FIG. 1 to apply an electric field over part of the peritoneal cavity of a subject;

FIG. 2D shows those array elements shared in the execution of firings illustrated in FIGS. 2A through 2C;

FIG. 2F shows a stretchable shirt that helps hold an array in place on a patient's skin while also allowing heat dissipation from the electrodes of FIGS. 1 and 2A-2D;

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
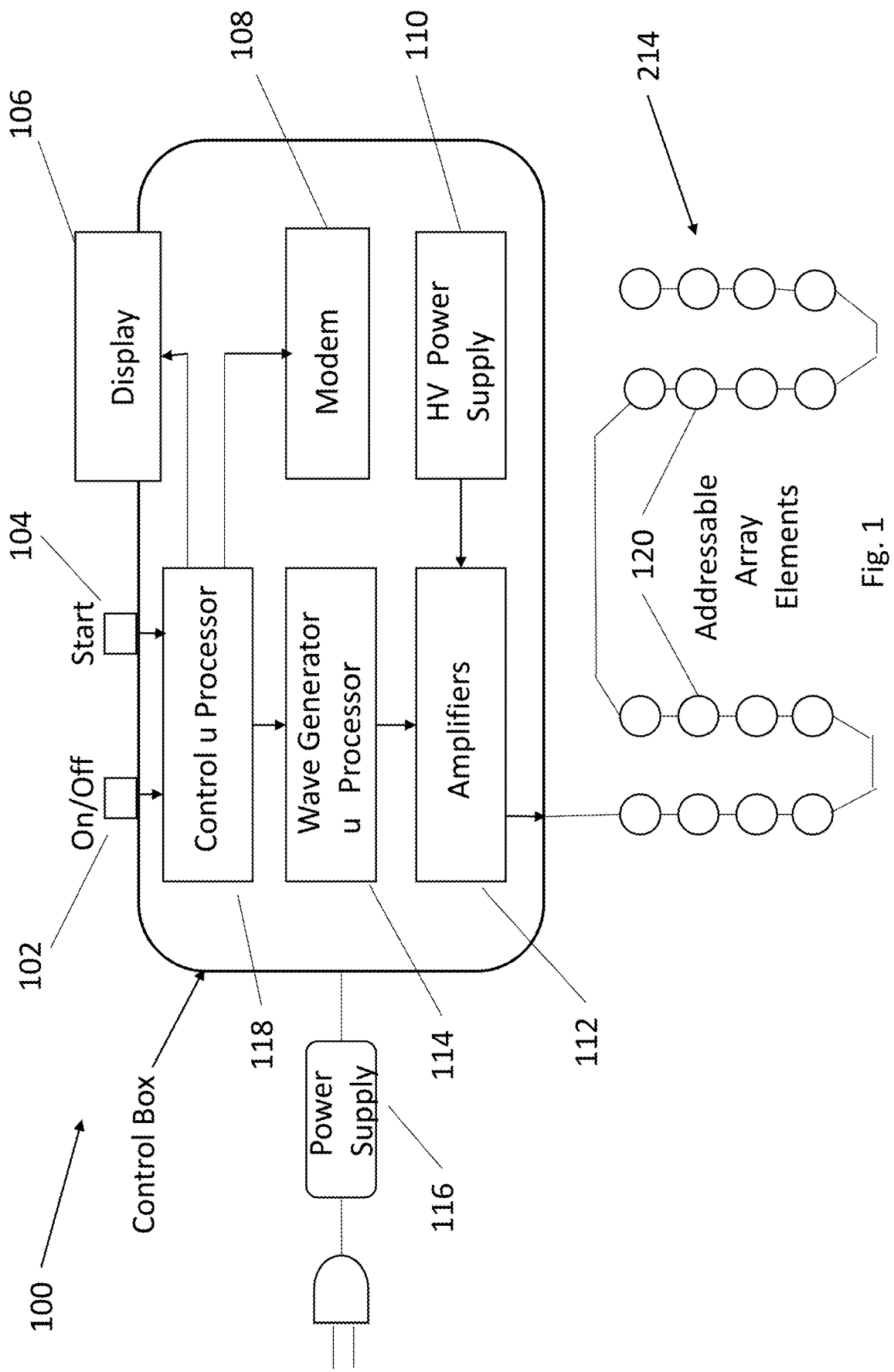
FIG. 1 shows a tumor treating system for creating sub arrays from a master array for applying electric fields to a subject using an embodiment of an electrode of the present invention.

Referring to the drawings and more particularly to FIG. 1 there is illustrated an embodiment of a tumor treating system 100 used to select sub arrays from a master array. An on/off switch 102 is coupled to the control box that does not start system 100 but enables system 100 to be started by a start switch 104. Once system 100 is started on/off switch 102 does however, act as a kill switch turning off system 100 any time pressed. System 100 contains a display screen 106 which gives a running status of system 100 and displays patient feedback messages to increase patient compliance such as number of hours used, etc.

The control box has a built-in modem 108 which is programmed to send usage data to a central server once per day. Modem 108 cannot be addressed from the outside. It will not respond to outside connection requests. Modem 108 can only send or receive data or instructions from a connection that it initiated, thereby increasing security.

A High Voltage Power Supply 110 converts 24 volts AC to 120 volts AC to power amplifiers 112 to generate sine waves used to create therapeutic electric fields through the body. Therapeutic electric fields that inhibit solid tumor growth have been established as those between 100 hKz and 500 hKz. These are commonly referred to as Tumor Treating Fields or TTFields. TTFields must be targeted through solid tumors at intensities of between 1 Vcm and 5 Vcm to have a tumor reduction effect.

Amplifiers 112 have a dedicated microprocessor 114 to control the generation of sine waves. The control box has a control processor 118 that carries out all functions, included, but not limited to temperature monitoring, communication with addressable arrays, voltage monitoring, modem function, display functions, etc.

Each array element 120 is an electrode 120 and each are addressable and programmable and can be paired with any other array element or number of array elements to create subarray pairs that provide the most advantageous coverage of a tumor on a subject. The system can share array elements for different tumor groups within the body as shown in FIGS. 2A-2D. For example, FIG. 2A as step 1 creates a subarray pair 202 over the liver front and back. Step 2, shown in FIG. 2B, creates a subarray 204 over the left lung. Step 3, in FIG. 2C, creates a subarray 206 over the peritoneal cavity. FIG. 2D shows those electrodes 120 that were shared in the creation of each of the subarray firings shown in FIGS. 2A through 2C.

Research shows that an electric field delivered over a tumor (at the right frequencies and intensities) intermittently, in short periods of time, are just as effective at reducing tumors as a constant field.

Prior art (not illustrated) attaches electrodes to patients using adhesive cloth coverings over the arrays. Surrounding each electrode, underneath the adhesive cloth, are foam supports (also not shown), that help hold the arrays in place. Both the foam supports and the adhesive cloth covering used to secure the arrays to the patient's body significantly slow the dissipation of heat from the entire array.

Figure 2E:
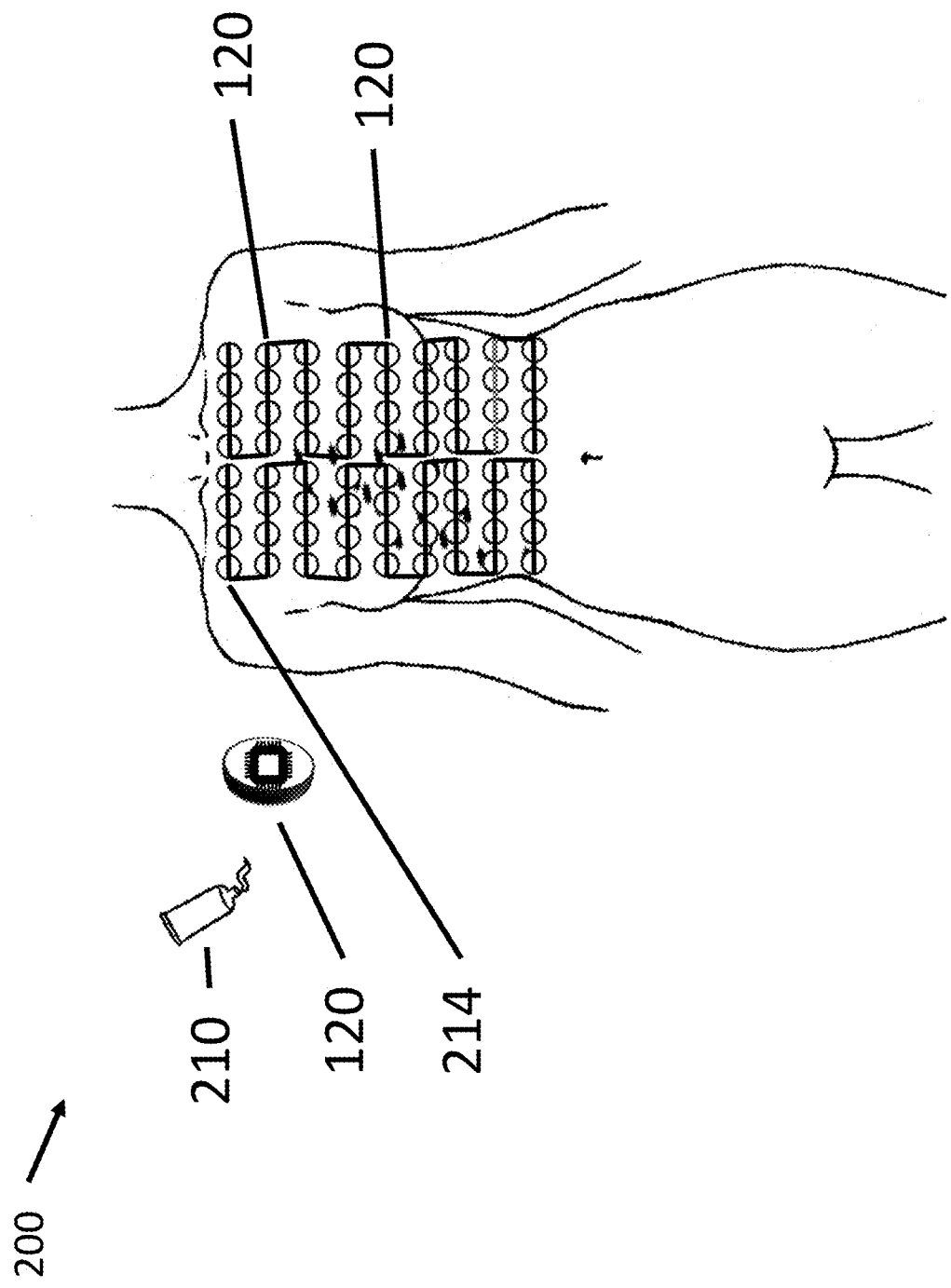
FIG. 2E shows a method of adhering arrays to a patient using medical adhesive that freely allows heat dissipation.

In contrast to the prior art, the present invention uses water soluble medical adhesive 210, as part of an electrode application system 200, shown in FIG. 2E, placed on the bottom of each electrode 120. The entire array 214 of electrodes 120 are then placed on the patient's skin held in place by the water-soluble medical adhesive. Unlike the prior art no adhesive coverings or support foam is needed.

If needed, as shown in FIG. 2F, a tight stretchable shirt 216 with breathable air holes throughout can be used to assist with holding arrays 214 in place. In addition, nonconductive clips 218 can be used to attach the arrays to the stretchable shirt for additional support. The result is a wearable array with significant direct air exposure to assist in heat dissipation.

Figure 3:
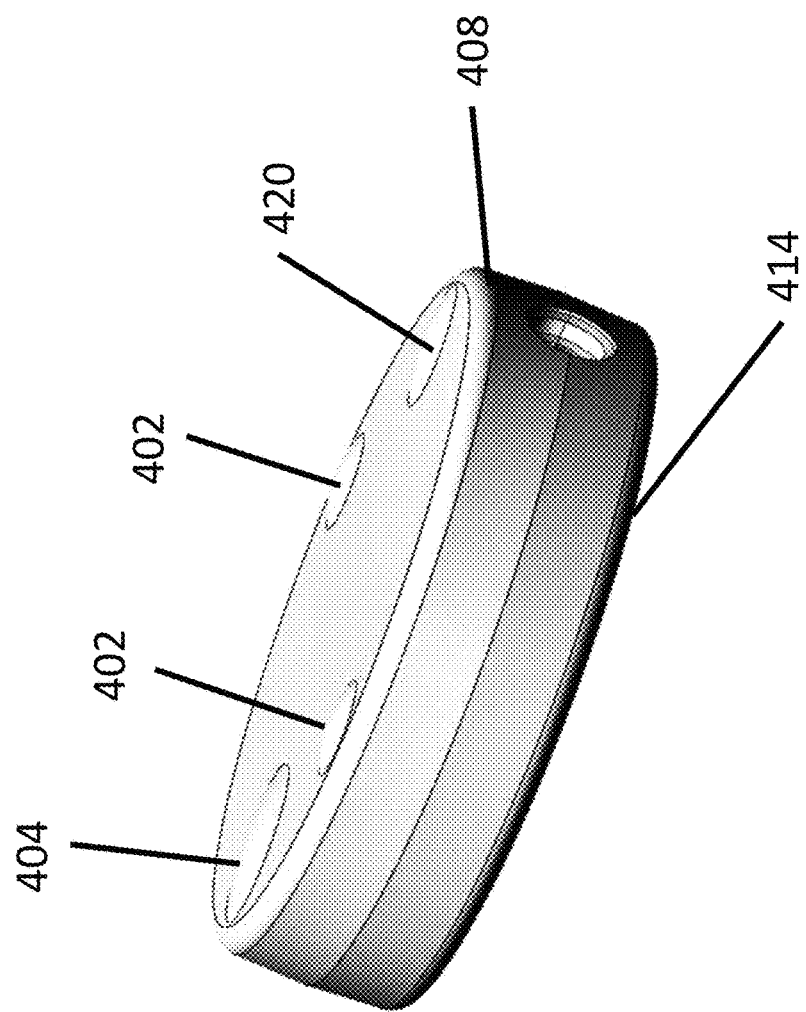
FIG. 3 shows an embodiment of a fully encapsulated insulated addressable electrode of the present invention used in FIGS. 1-2F.

FIG. 3 illustrates a fully encapsulated, thermally conductive, independently electrically addressable, programable insulated electrode 120. The preferred method of wiring each electrode 120 to each other to form an array 214, is to use discrete twisted pairs (not shown, for the sake of clarity) to block interference to wires dedicated to communication between electrodes 120. Although it is contemplated that many forms of wiring can be applied, including, but not limited to, continuous twisted pair, and flex circuits. Electrodes 120 are wired together to form large arrays 214 as shown in FIG. 2A (usually up to 1000 electrodes). When an electrode 120 is part of an array it may be referred to as an Array Element 120.

Figure 4A:
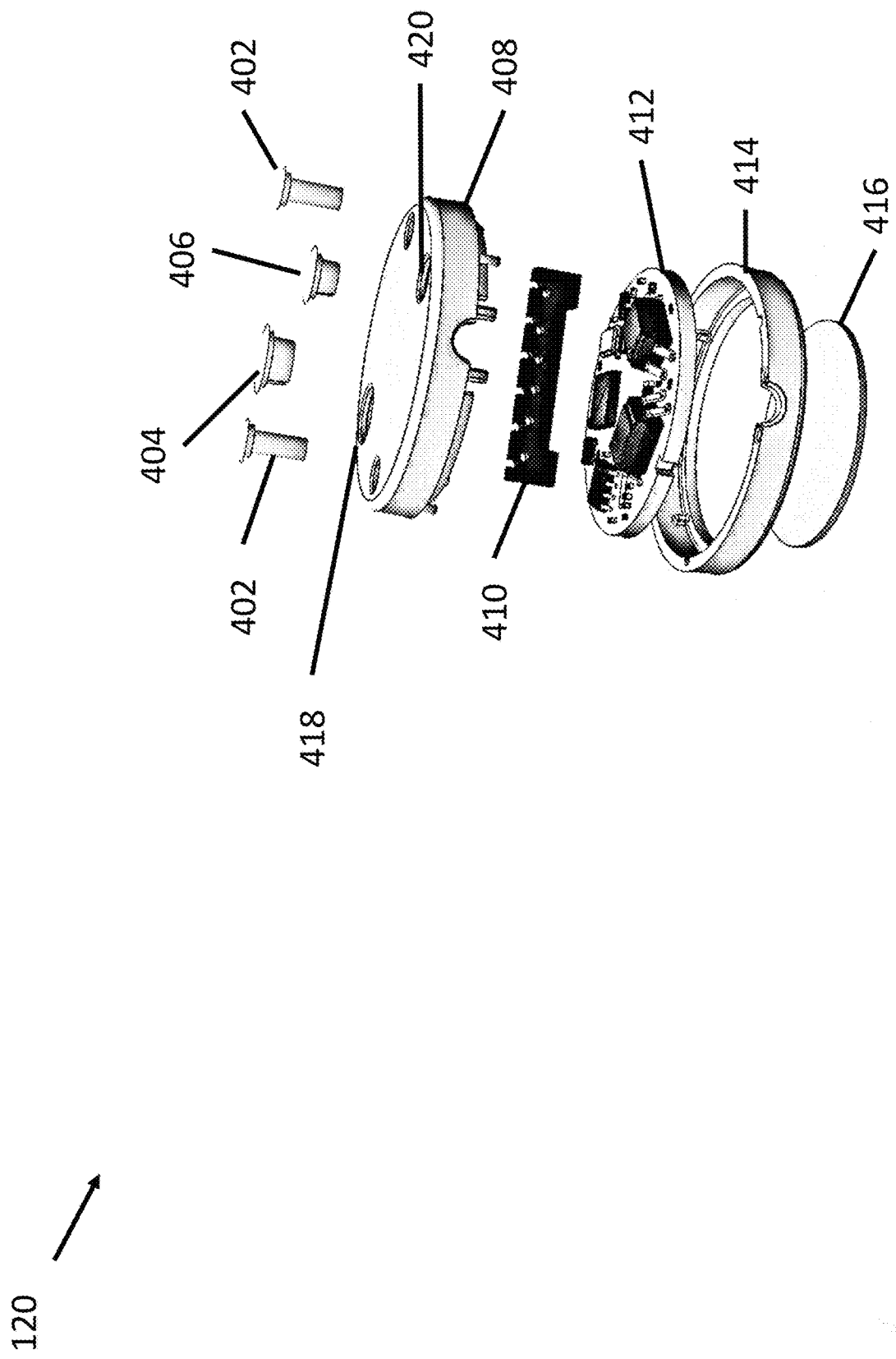
FIG. 4A shows an exploded view of the fully encapsulated insulated addressable electrode of FIG. 3.

FIG. 4A shows an exploded view of electrode 120 shown in FIG. 3. The challenge during tumor treating field therapy is to keep the temperature of each electrode at a comfortable level for the patient. This is generally less than 105 degrees F., and preferably 101° F. or below. Prior art forms of TTField systems are poor at dissipating heat from electrodes. These systems typically throttle back the intensity of the electric field to thereby lower the heat generated in those electrodes. However, this method also lowers the ability of the system to reduce tumors in patients.

To overcome the problem of overheating the present electrode 120 is constructed from and fully encapsulated with thermally conductive materials throughout. Each material has a thermal conductivity of 20 BTU-in/Hr. $Ft^{2o}$ F. or higher. A thermally conductive top cover 408 is constructed from material that has a thermal conductivity of 20 (BTU-in/Hr. $Ft^{2o}$ F.) or higher, such as CoolPoly® series D & E. The stack up shown in FIG. 4A seeks to have the thermal conductivity of each layer from the top (or outer layer) be equal to or greater than the layer below. This allows for optimal heat dissipation.

Meeting the thermal conductivity requirements mentioned above is a specially designed thermally conductive printed circuit board 412. Examples of these materials include Tlam™ and Tpreg™ thermally conductive printed circuit boards. Board 412 is 3 to 5 times more thermally conductive than standard printed circuit board material. Shown on board 412 are components that are placed in each and every electrode 120. These include thermistors, microprocessors, oscillators, CAN bus communication components, relays, led lights, magnetic switches, and other components.

Figure 4B:
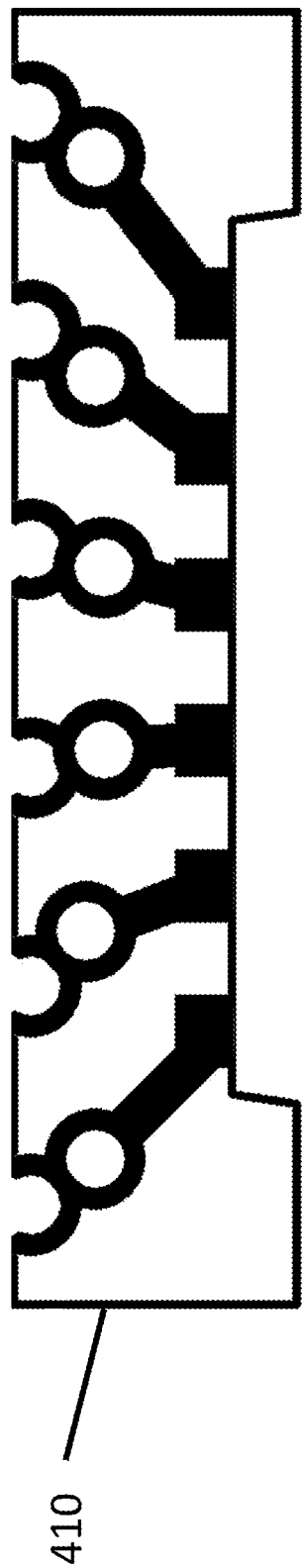
FIG. 4B shows a close up view of a wiring bridge from FIG. 4A.

To facilitate the wiring of one electrode 120 to the next, a wiring bridge 410 is soldered in place as illustrated in FIG. 4B. The wiring bridge 410 contains a series of holes with half holes connected to each via copper traces. The ingress discrete wires (not shown, for the sake of clarity) are soldered into the full holes. The egress wires are placed in the half wholes (also, not shown for the sake of clarity). The trace from the full hole continues down to be soldered to the main printed circuit board 412.

Figure 5:
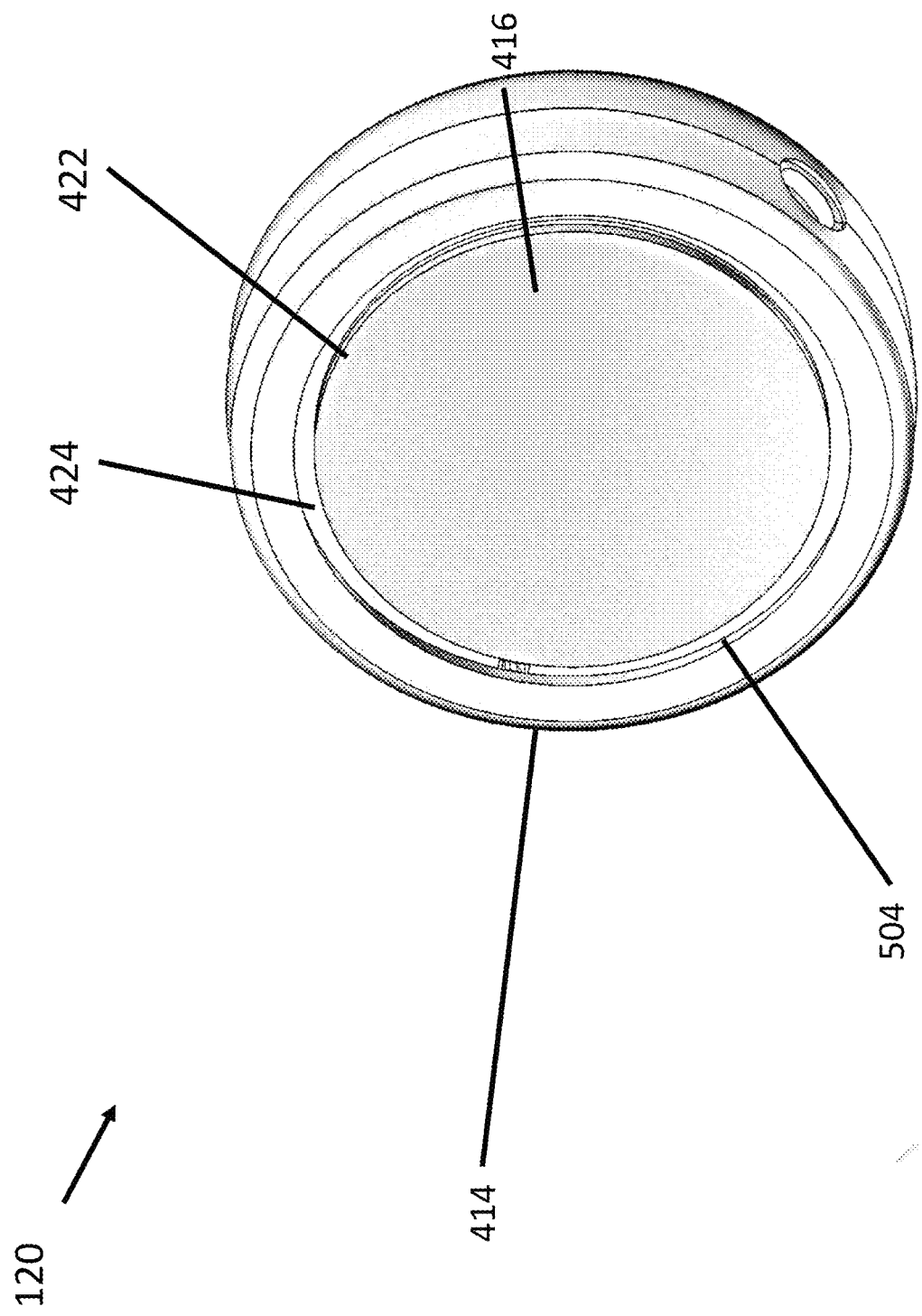
FIG. 5 is a perspective bottom view of the fully encapsulated insulated addressable electrode from FIG. 3, emphasizing the moat around the insulation layer.
Figure 6:
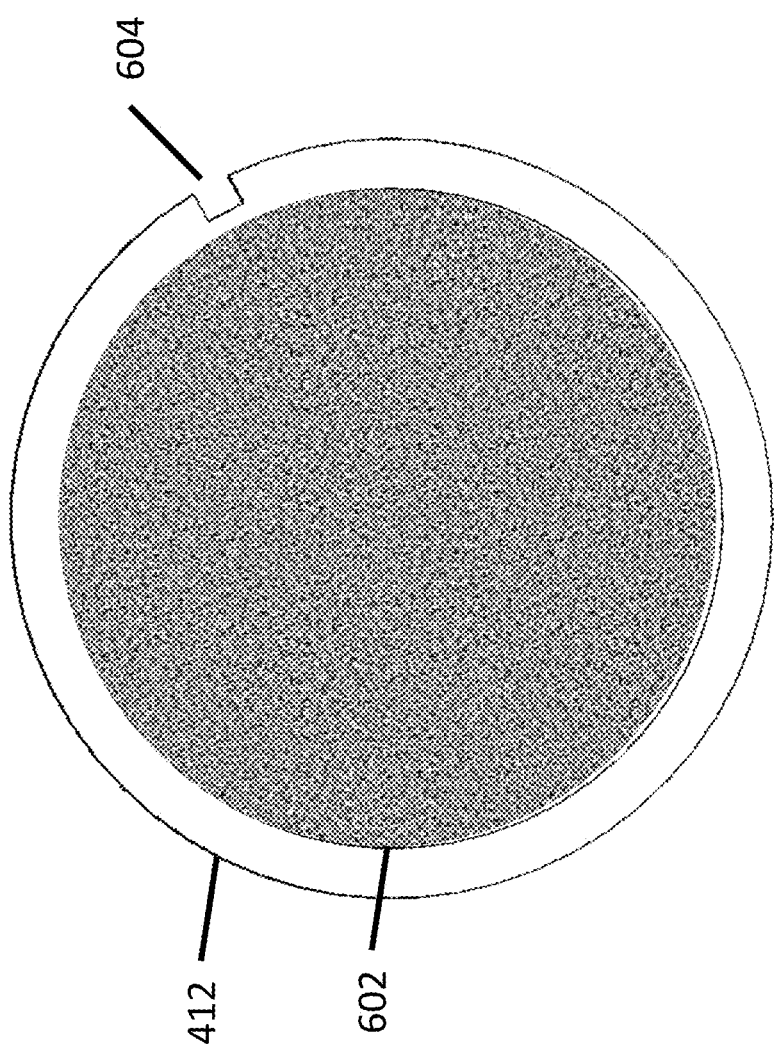
FIG. 6 is a bottom view of a printed circuit board within the encapsulated insulated addressable electrode shown in the exploded view of FIG. 4.

On the bottom of each printed circuit board 412 an insulator 416 is attached. In this case a ceramic disk 416 shown in FIG. 5. One advantage of insulator 416 is their larger size, between 20 mm and 30 mm in diameter, than the prior art. This allows for heat dissipation over a much larger area than the prior art. Each insulator 416 is a ceramic layer 416, which has a metalized layer 422 on the top side (opposite to that shown in FIG. 5). In FIG. 6 there is shown a copper layer 602 on the bottom of the printed circuit board 412. The copper layer 602 is equal or slightly larger in size and shape to ceramic disk 416 with metalized layer 422.

The attachment of metalized layer 422 to copper layer 602 is achieved via a continuous solder layer therebetween also substantially equal to the size and shape of the ceramic disk 416 and copper plate 602. This creates a 100% or nearly 100% area bond between metalized layer 422 of ceramic insulator 416 and printed circuit board 412 allowing maximum heat transfer. The soldering bond is achieved in a reflow process that allows metalized layer 422 of ceramic disk 416 to center itself due to surface tension.

Figure 7:
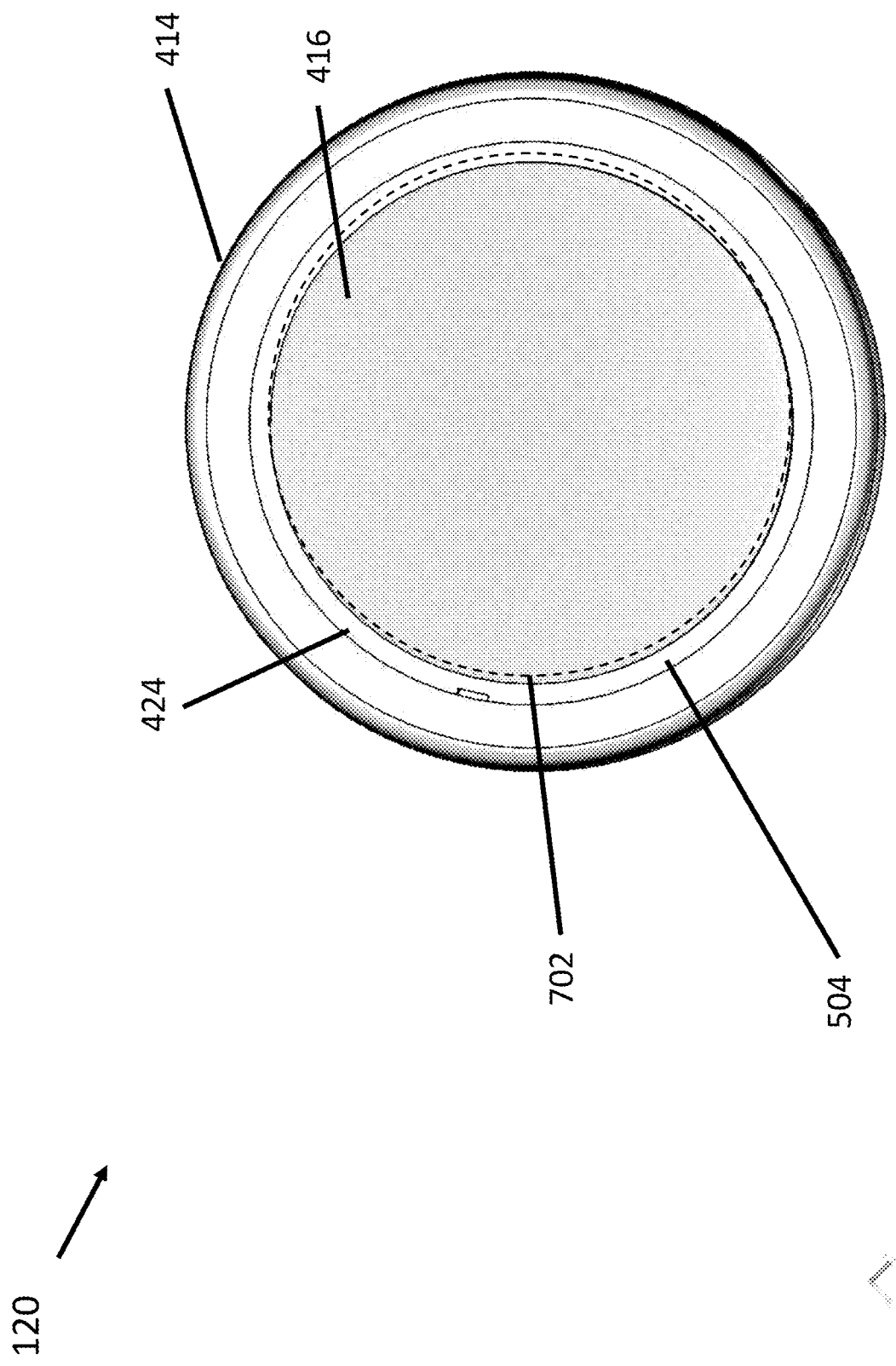
FIG. 7 is a bottom view of the encapsulated insulated addressable electrode, illustrating the placement tolerance margin moat design of the electrode.

One of the challenges in achieving the continuous 100% contact between the metalized side 422 of ceramic insulator 416 and the bottom of the printed circuit board 412 is drifting of ceramic disk 416 over copper plate 602 on the bottom of printed circuit board 412 during the reflow solder process (shown by the dotted line 702 in FIG. 7). To mitigate this problem a moat 424 or margin space 424 has been designed into the bottom section 414 of encapsulation 504. This allows a large tolerance for drifting in any direction. Once completed moat 424 is filled with insulative UV glue or epoxy or similar substance.

The goal of forming an electric field through the human body using an array is to have each side of the array pair mimic a solid plate as much as possible. Piezo ceramic disk research has shown that energizing a metalized disk from a single point (lead) generates more current around the point than the disk as a whole. This indicates that energizing the entire metalized layer 422 at once will form a more uniform electric field as coupling occurs through the ceramic disk 416. Thereby more closely mimicking a solid plate.

Ceramic disk 416 is the source of heat during therapy. As a part of this invention simulations have been run to determine a ceramic formula that balances high dielectric constant with minimal heat storage. The result is a unique ceramic thermal conductive insulator 416.

Figure 8B:
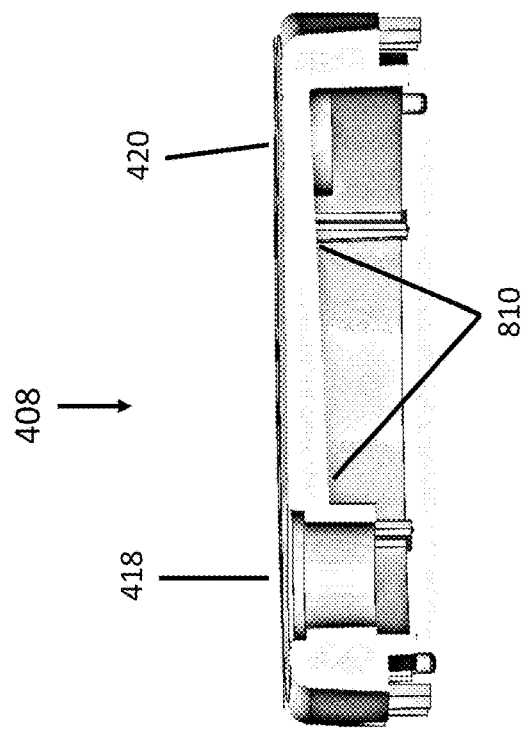
FIG. 8B is a cross-sectional view of the top section of the electrode of FIG. 3 and is taken along line 8-8.
Figure 8A:
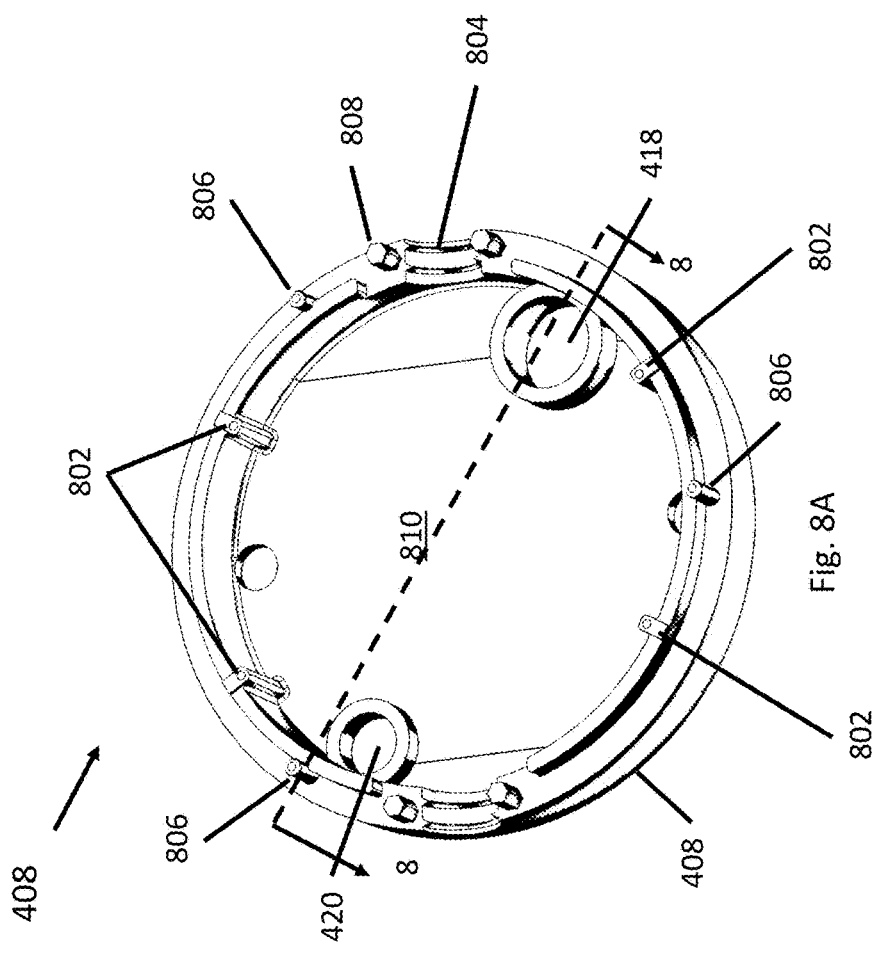
FIG. 8A is a perspective illustration of the top section of the encapsulated electrode shown in FIG. 3.
Figure 8C:
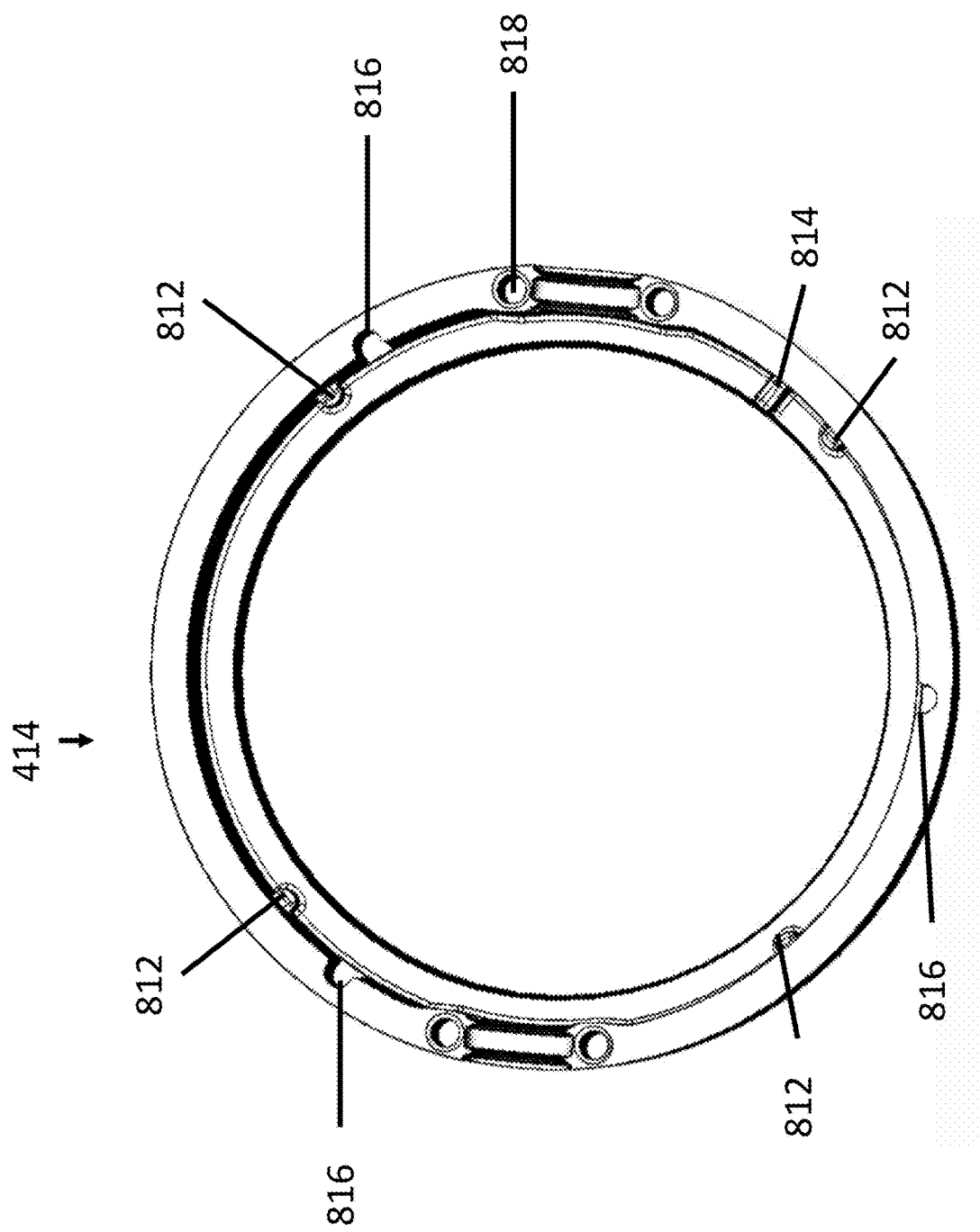
FIG. 8C illustrates the bottom section of the encapsulated electrode shown in FIG. 3.

To understand the joining of all components shown in FIG. 4A the features of a top component 408 is shown in FIG. 8A and FIG. 8B and the unique features of bottom component 414 is shown in FIG. 8C.

Top component 408 shown in FIG. 8A has 4 protrusions 802 that press down on a printing circuit board 412 holding it downward. This sandwiches printed circuit board 412 between corresponding protrusions 812 of bottom component 414. This alignment secures printed circuit board 412 in place allowing a small area of space 360 degrees around board 412 for the potting material to flow. This ensures a waterproof seal around printed circuit board 412.

In addition, printed circuit board 412 contains a slot 604 shown in FIG. 6. Slot 604 lines up with the protrusion on bottom section 814, thereby registering it in place.

Top component 408 shown in FIG. 8A also has 3 male protrusions on an outer edge 806. When top component 408 is joined with bottom component 414 they line up and insert into 3 slots on bottom 816. This mandates that top 408 and bottom 414 can only be joined in one way preventing misalignment of other components.

In FIG. 8B a fill hole 418 for the thermal conductive potting material is shown. Opposite fill hole 418 is an air escape hole 420 that facilitates displacing all internal air within electrode 120, enhancing thermal conductivity. In between fill hole 418 and air escape hole 420 a slanted ceiling 810 of top component 408 is shown that further aids air to escape as the cavity is filled with thermal conductive potting material.

In FIG. 8A sealing ribs 804 are shown. These ribs 804 push against the outer insulation layer of the ingress and egress wires when top component 408 and bottom component 414 are joined creating a seal that allows the potting material to form a waterproof seal as it cures.

Also, on FIG. 8A there is illustrated male connecting pins 808, these are inserted into corresponding female positions 818 shown in FIG. 8C which enable a tight connection between top component 408 and bottom component 414.

Once top 408, bottom 414, ceramic disk 416, and all sections of the encapsulation are in place, light pipes are placed above the LEDs by inserting them in holes on top cover 402. The light pipes funnel the light from the LEDs to the surface for viewing. The bottom of the light pipes (not shown) have a rounded cavity at the bottom that covers the LEDs. This creates a seal around the LEDs to the printed circuit board preventing potting material from blocking light from the LEDs.

Once all components of board 412 are in place a thermal conductive potting material, such as "Duralco 128", is poured into fill hole 418 on the top cover until it fills to air hole 420. Once full, caps are placed over fill hole 404 and air holes 406, held in place by the curing of Duralco 128. The result is a continuous thermally conductive electrode throughout its construction.

Figure 9:
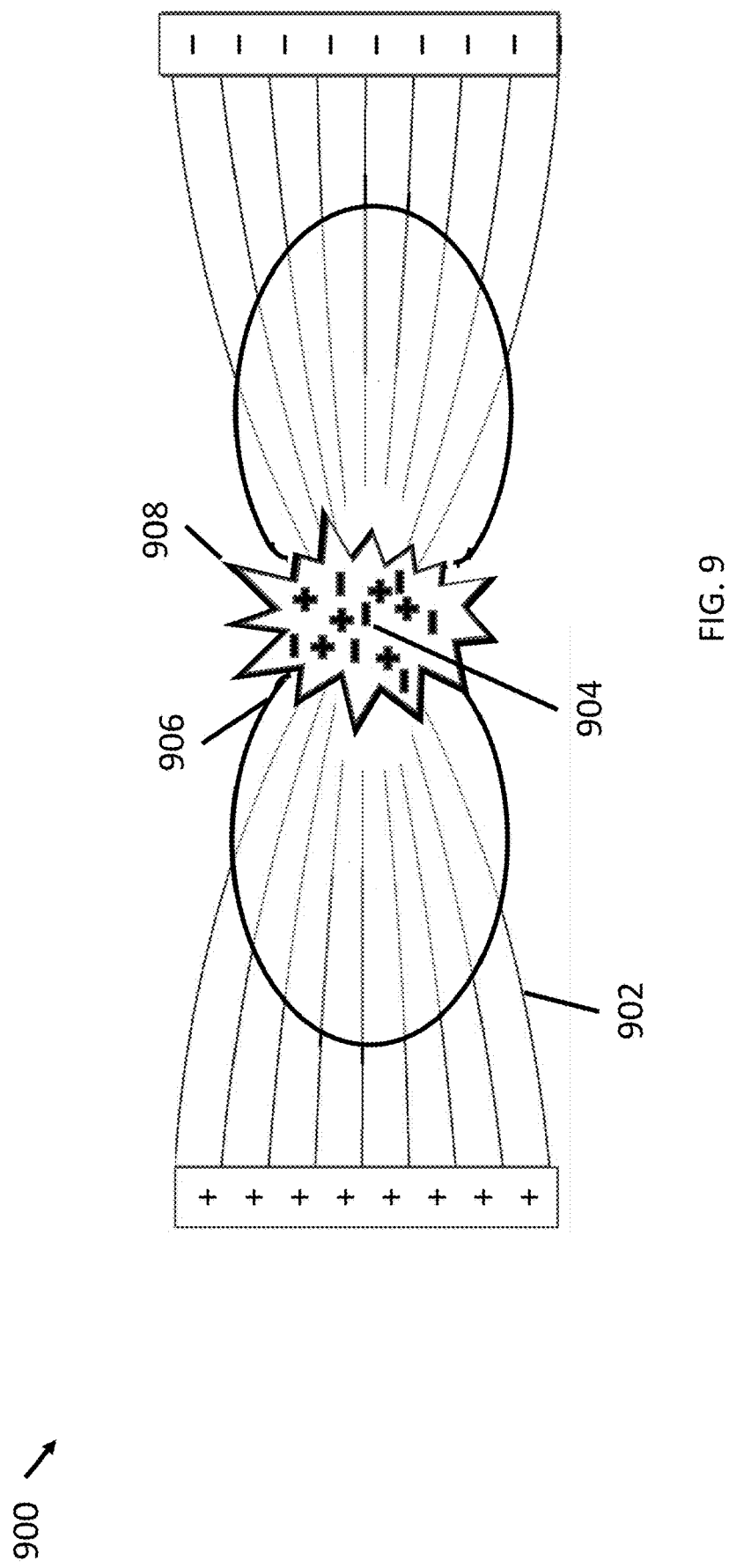
FIG. 9 shows the phenomenon called dielectrophoresis.

In FIG. 9 there is shown a phenomenon called Dielectrophoresis. This occurs when an electric field 902 lines up with the cleavage furrow of a dividing tumor cell 906 during telophase. Polarizable objects 904 are pulled toward the highest concentration of electric field, in this case, the genetic material needed for cell division. This causes targeted cancer cells to disintegrate at cleavage furrow 908.

Figure 10:
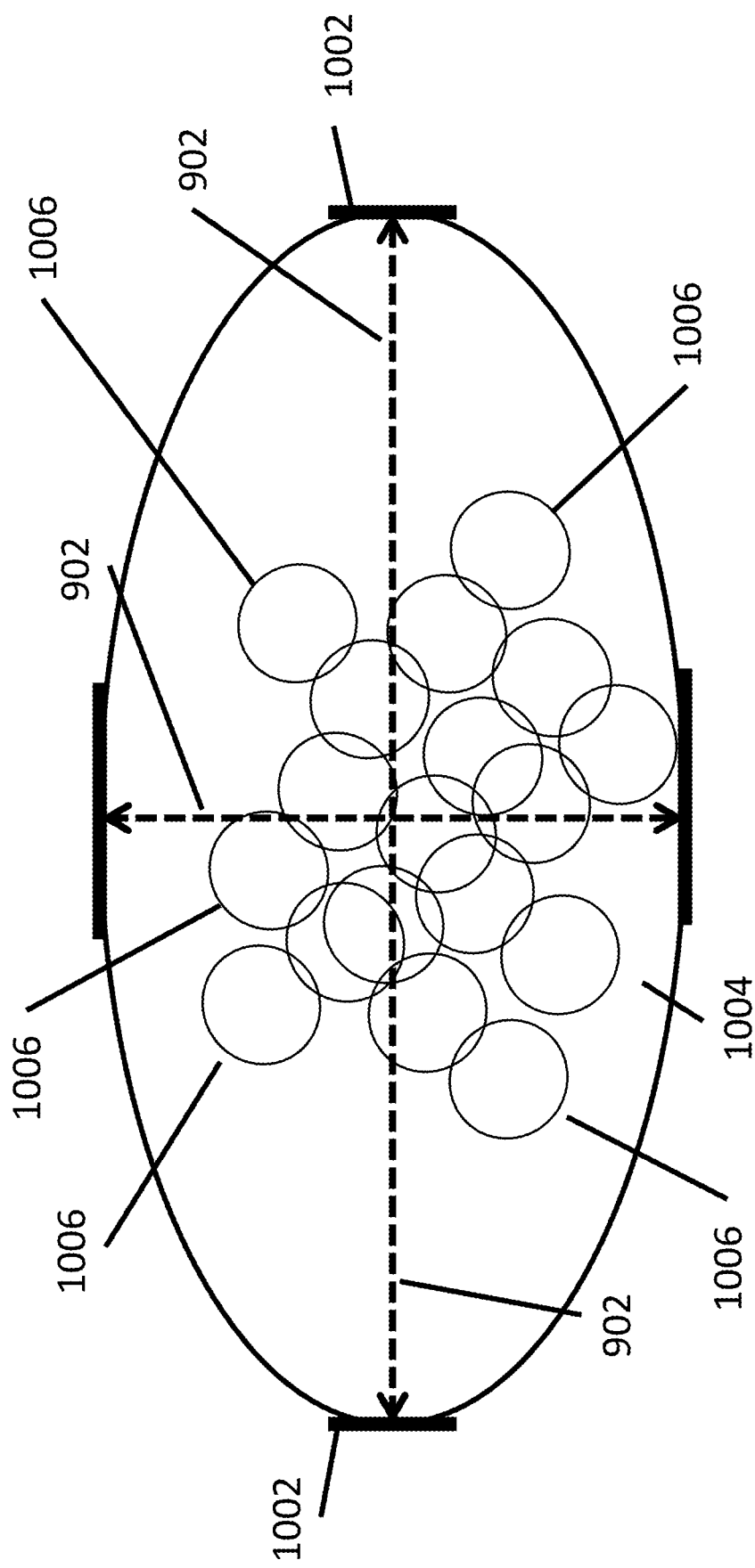
FIG. 10 shows prior art electric fields delivered from arrays in which all electrode array elements can only act as a group (all on or all off), array electrodes are not individually addressable and programable thereby limiting possible angles of electric field delivery.

FIG. 10 shows electric fields 902 delivered from arrays in which all electrode array elements 1002 can only act as a group (all on all off). In this prior art system, array electrodes 1002 are not individually addressable and programable thereby limiting possible angles of electric field delivery over a tumor 1004. This misses opportunities to cause dielectrophoresis in cells 1006. In FIG. 10 each of the cells represented are in the telophase of mitosis. None of the angles formed cause a nonuniform field through most of cells 1006. Fixed Array TTF of the prior art misses many opportunities to take advantage of dielectrophoresis because of the limited number of angles to which it can deliver electric fields.

Figure 11:
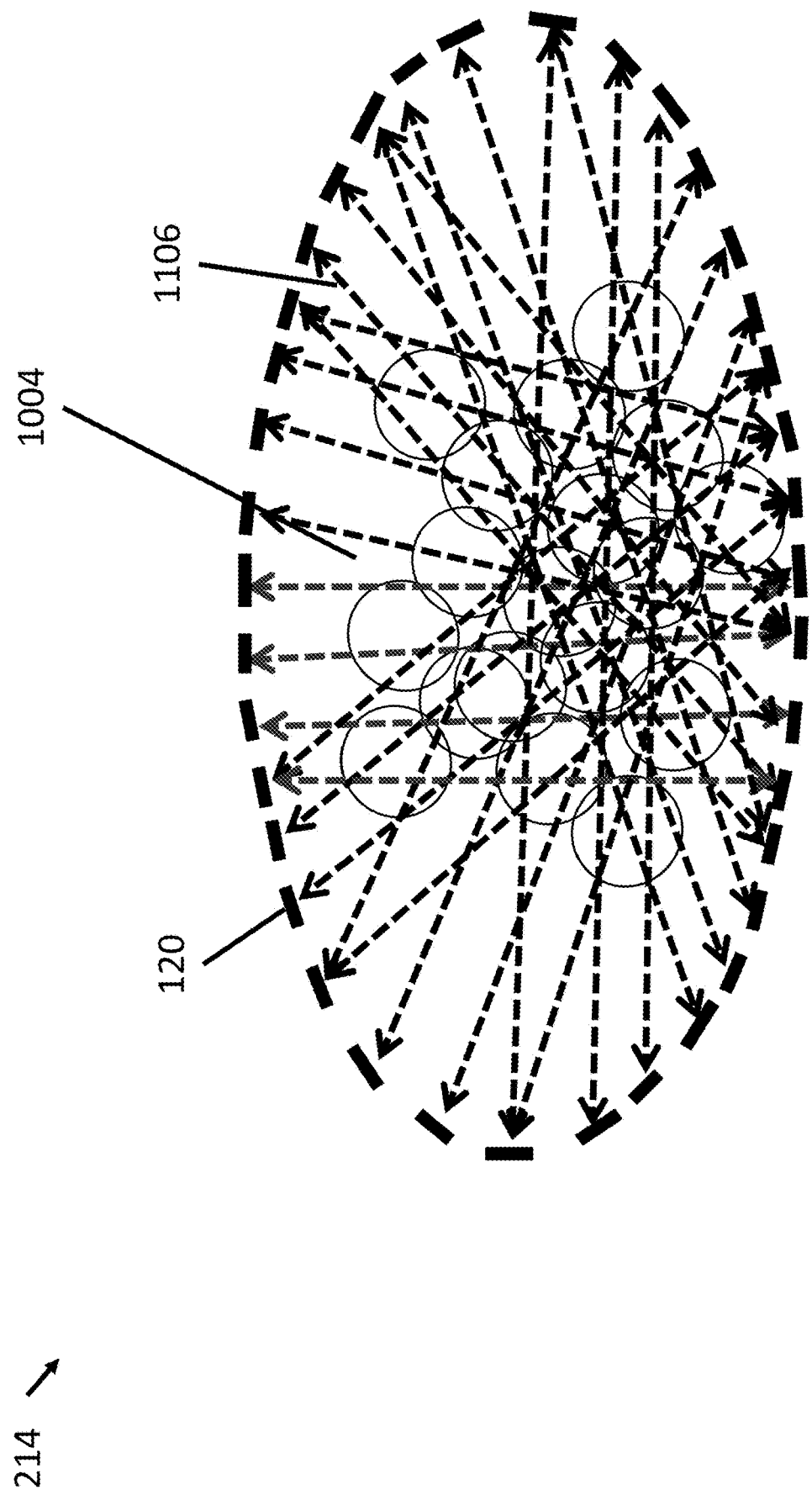
FIG. 11 shows how individually addressable and programable electrodes of the present invention create a large number of delivery angles for electric field therapy.

FIG. 11 shows how individually addressable and programable electrodes 120 can create a large number of delivery angles 1106 for electric field therapy over a tumor 1004. Thereby creating more opportunity for dielectrophoresis to take place. This represents one of the advantages of the present invention, in that the present invention is much more likely to cause dielectrophoresis than fixed field TTF of the prior art, because of the many angles available through dynamic reassignment of array elements and how this more effectively orients the electromagnetic fields in the reproducing cancer cells.

Use of the term "array" herein has taken different meanings, dependent upon context. In one sense when talking about the grouping of electrodes on the body it is broadly referring to the physical rows and columns of the electrodes, or at least their placement, whether in rows and columns or not. The arrays that are used in forming electromagnetic fields are dynamically selected so that the desired field can be generated and this means a subset of the electrodes that may or may not be adjacent are selected and used.

Tumor treating system 100 is used for the delivery of tumor treating electric fields to a patient includes a control device 118, a field generator 114 and electrodes 120. Control device 118 has a frequency range, a firing configuration and a firing sequence. The field generator 114 generates electrical signals within the frequency range. Electrodes 120 are placed in optimized locations on the patient. Each electrode 120 includes a ceramic layer 416, a metalized layer 422 and a circuit element 412. The metalized layer 422 coupled to ceramic layer 416 on one side of ceramic layer 416, metalized layer 422 having an outer surface facing away from ceramic layer 416. Circuit element 412 being coupled to metalized layer 422, the coupling of metalized layer 422 to circuit element 412 being across substantially all of the outer surface of metalized layer 422, circuit element 412 conducting the electrical signals from field generator 114 to metalized layer 422 as directed by control device 118.

Each electrode 120 further includes a moat 424 within which metalized layer 422 is coupled to circuit element 412. Moat 424 extends radially outward from metalized layer 422 and moat 424 is thermally conductive. Circuit element 412 is coupled to metalized layer 422 by way of solder, with the solder extending outward substantially to where moat 424 on circuit element 412 begins. Moat 424 is radially outside of ceramic layer 416.

It is also contemplated that less than the full area of the metalized conductor can be in direct electrical contact with the circuit 412. The gap(s) not connected electrically to the circuit element 412 can be filled with a thermally conductive, electrically insulative material, for example, Durelco potting material, thermally conductive tape, adhesive, paste, or the like.

In another embodiment of the present invention the metalized layer 422 is coupled to the circuit element 412 using a plurality of conductors. These could be soldered or connectorized connections. It is typically desirable to have more than one point on the metalized conductor energized electrically since this reduces the piezo and other transient effects in the ceramic insulator 416. While a single point can be used, it is desirable to have a plurality of electrical couplings positioned across the metalized layer such that the metalized layer 422 is energized evenly across its surface. This contemplated embodiment will reduce the total weight of the solder used which will lower the overall weight of the electrode arrays worn by the patient.

To ensure that the heat generated by the metalized ceramic element is dissipated efficiently substantially all of the surface of the metalized layer 422 that is not in electrical contact with the circuit element 412 will be thermally coupled to the circuit element 412 via a thermally conductive filler. The filler could be a thermal pad or tape, thermally conductive potting material such as Durelco or similar, thermal grease or adhesive, etc.

A circuit element 412 is coupled to the metalized layer 422, the coupling of the metalized layer 422 to the circuit elements 412 being from one or more electrically conductive connections that energize the surface of the metalized layer 422 in a substantially uniform manner. The circuit element 412 is thermally coupled to the metalized layer 422 with a thermally conductive material across substantially all of the outer surface of the metalized layer 422 not in electrical connection to the circuit element, the circuit element 412 conducting the electrical signals from the field generator to the metalized layer as directed by the control device.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and is claimed in the claims.

What is claimed is:

1. A tumor treating system for the delivery of tumor treating electric fields to a patient, comprising:
   a control device with a frequency range, a firing configuration and a firing sequence;
   a field generator generating electrical signals within the frequency range;
   a plurality of electrodes placed in optimized locations on the patient, each of the electrodes including:
   a ceramic layer;

a metalized layer coupled to the ceramic layer on one side of the ceramic layer, the metalized layer having an outer surface facing away from the ceramic layer;

a circuit element being coupled to the metalized layer, the coupling of the metalized layer to the circuit element being across substantially all of the outer surface of the metalized layer, the circuit element conducting the electrical signals from the field generator to the metalized layer as directed by the control device; and a moat within which the metalized layer is coupled to the circuit element, the circuit element being electrically coupled to the metalized layer with a solder, the circuit element being additionally thermally coupled to the metalized layer by way of a thermally conductive material, the thermally conductive material extending outward from the metalized layer to where the moat begins.

2. The tumor treating system of claim 1, wherein the moat is filled with one of an UV glue and an epoxy.

3. The tumor treating system of claim 2, wherein the moat extends radially outward from the metalized layer.

4. The tumor treating system of claim 3, wherein the moat is thermally conductive.

5. The tumor treating system of claim 1, wherein the moat is radially outside of the ceramic layer.

6. The tumor treating system of claim 5, further comprising a thermally conductive potting separately encapsulating the circuit element of each electrode.

7. Electrodes for use with a tumor treating system for the delivery of tumor treating electric fields to a patient, the tumor treating system including a control device with a frequency range, a firing configuration and a firing sequence for the electrodes, a field generator generating electrical signals within the frequency range, each of the electrodes being placed in optimized locations on the patient, each of the electrodes comprising:

a ceramic layer;

a metalized layer coupled to the ceramic layer on one side of the ceramic layer, the metalized layer having an outer surface facing away from the ceramic layer; and a circuit element being coupled to one of the metalized layer, the coupling of the metalized layer to the circuit element being across substantially all of the outer surface of the metalized layer, the circuit element conducting the electrical signals from the field generator to the metalized layer as directed by the control device; and a moat within which the metalized layer is coupled to the circuit element, the circuit element being electrically coupled to the metalized layer with a solder, the circuit element being additionally thermally coupled to the metalized layer by way of a thermally conductive material, the thermally conductive material extending outward from the metalized layer to where the moat begins.

8. The electrodes of claim 7, wherein the moat is filled with one of an UV glue and an epoxy.

9. The electrodes of claim 8, wherein the moat extends radially outward from the metalized layer and the ceramic layer.

10. The electrodes of claim 9, wherein the moat is thermally conductive.

11. The electrodes of claim 10, wherein the moat is radially outside of the ceramic layer.

12. The electrodes of claim 11, further comprising a thermally conductive potting separately encapsulating each of the circuit elements.

13. A method of using electrodes to deliver tumor treating electric fields to a patient, comprising the steps of:

placing a plurality of the electrodes in optimized locations on the patient, each of the electrodes being independently programmable, the optimized locations are selected relative to a target area wherein at least one tumor is located, each electrode including:

a ceramic layer;

a metalized layer coupled to the ceramic layer on one side of the ceramic layer, the metalized layer having an outer surface facing away from the ceramic layer; and a circuit element being coupled to the metalized layer, the coupling of the metalized layer to the circuit element being across substantially all of the outer surface of the metalized layer, the circuit element conducting the electrical signals from the field generator to the metalized layer as directed by the control device, a moat within which the metalized layer is coupled to the circuit element, the circuit element being electrically coupled to the metalized layer with a solder, the circuit element being additionally thermally coupled to the metalized layer by way of a thermally conductive material, the thermally conductive material extending outward from the metalized layer to where the moat begins; and programming a control device with a frequency range, a firing configuration and a firing sequence for the plurality of electrodes; and generating electrical signals in the frequency range, the electrical signals being directed to at least two of the electrodes in a sequence determined by the firing sequence.

14. The method of claim 13, wherein the moat is filled with one of an UV glue and an epoxy.

15. The method of claim 14, wherein the moat extends radially outward from the metalized layer.

16. The method of claim 15, wherein the moat is thermally conductive.

* * * * *